(12) United States Patent
Sun et al.

(10) Patent No.: US 8,299,297 B2
(45) Date of Patent: Oct. 30, 2012

(54) PROCESS FOR THE PRODUCTION OF GLYCOLIC ACID

(75) Inventors: Ying Sun, Liaoning (CN); Hua Wang, Liaoning (CN); Zhongmin Liu, Liaoning (CN)

(73) Assignees: Dalian Institute of Chemical Physics, Chinese Academy of Sciences, Liaoning (CN); BP P.L.C., London (GB)

( * ) Notice: Subject to any disclaimer, the term of this patent is extended or adjusted under 35 U.S.C. 154(b) by 0 days.

(21) Appl. No.: 12/736,882

(22) PCT Filed: May 20, 2008

(86) PCT No.: PCT/CN2008/000971
§ 371 (c)(1),
(2), (4) Date: Feb. 10, 2011

(87) PCT Pub. No.: WO2009/140788
PCT Pub. Date: Nov. 26, 2009

(65) Prior Publication Data
US 2011/0166383 A1    Jul. 7, 2011

(51) Int. Cl.
*C07C 51/10*    (2006.01)
*C07C 59/06*    (2006.01)
*C07C 27/06*    (2006.01)

(52) U.S. Cl. .......... 562/518; 562/579; 568/864

(58) Field of Classification Search .......... None
See application file for complete search history.

(56) References Cited

U.S. PATENT DOCUMENTS

| | | | | |
|---|---|---|---|---|
| 2,152,852 A * | 4/1939 | Loder | .......... | 562/518 |
| 2,153,064 A | 4/1939 | Larson | | |
| 2,285,448 A * | 6/1942 | Loder | .......... | 568/864 |
| 3,911,003 A | 10/1975 | Suzuki | | |
| 6,376,723 B2 * | 4/2002 | Drent et al. | .......... | 568/864 |

FOREIGN PATENT DOCUMENTS

| | | |
|---|---|---|
| DE | 3 107 518 | 12/1981 |
| DE | 31 07 518 A1 | 12/1981 |
| EP | 0 114 657 | 8/1984 |
| WO | WO 01/48644 A1 | 7/2001 |
| WO | WO 01/49644 A1 | 7/2001 |

OTHER PUBLICATIONS

International Search Report for PCT/CN2008/000971, mailed Feb. 19, 2009.
Written Opinion for PCT/CN2008/000971, mailed Feb. 19, 2009.
He, Dehua, et al; "Condensation of formaldehyde and methyl formate to methyl glycolate and methyl methoxy acetate using heteropolyacids and their salts"; *Catalysis Today*, vol. 51, pp. 127-134 (1999).
"Catalysis by Polyoxometalates"; *Catalysts for Fine Chemical Synthesis*, vol. 2, edited by Ivan Kozhevnikov, Springer-Verlag, Berlin, 21 pgs (2003).
Reddy, K.M., et al; "Acidity Constants of Supported Salts of Heteropoly Acids Using a Methodology Related to the Potentiometric Mass Titration Technique"; *Journal of Solution Chemistry*, vol. 35, No. 3; pp. 407-423 (2006).
Fumin, Zhang, et al; "Catalytic performances of heteropoly compounds supported on dealuminated ultra-stable Y zeolite for liquid-phase esterification"; *Science in China: Series B Chemistry*, vol. 49, No. 2, pp. 140-147 (2006).
Drago, R.S., et al; "An Acidity Scale for Bronsted Acids Including $H_3PW_{12}O_{40}$"; *J. Am. Chem.. Soc.*, vol. 119, pp. 7702-7710 (1997).

* cited by examiner

*Primary Examiner* — Paul A Zucker
(74) *Attorney, Agent, or Firm* — Nixon & Vanderhye

(57) ABSTRACT

Process for the production of glycolic acid by contacting carbon monoxide and formaldehyde with a catalyst containing an acidic polyoxometalate compound encapsulated within the pores of a zeolite. The zeolite has cages larger than the acidic polyoxometalate compound, and has pores with a diameter smaller than the diameter of the acidic polyoxometalate compound.

12 Claims, 1 Drawing Sheet

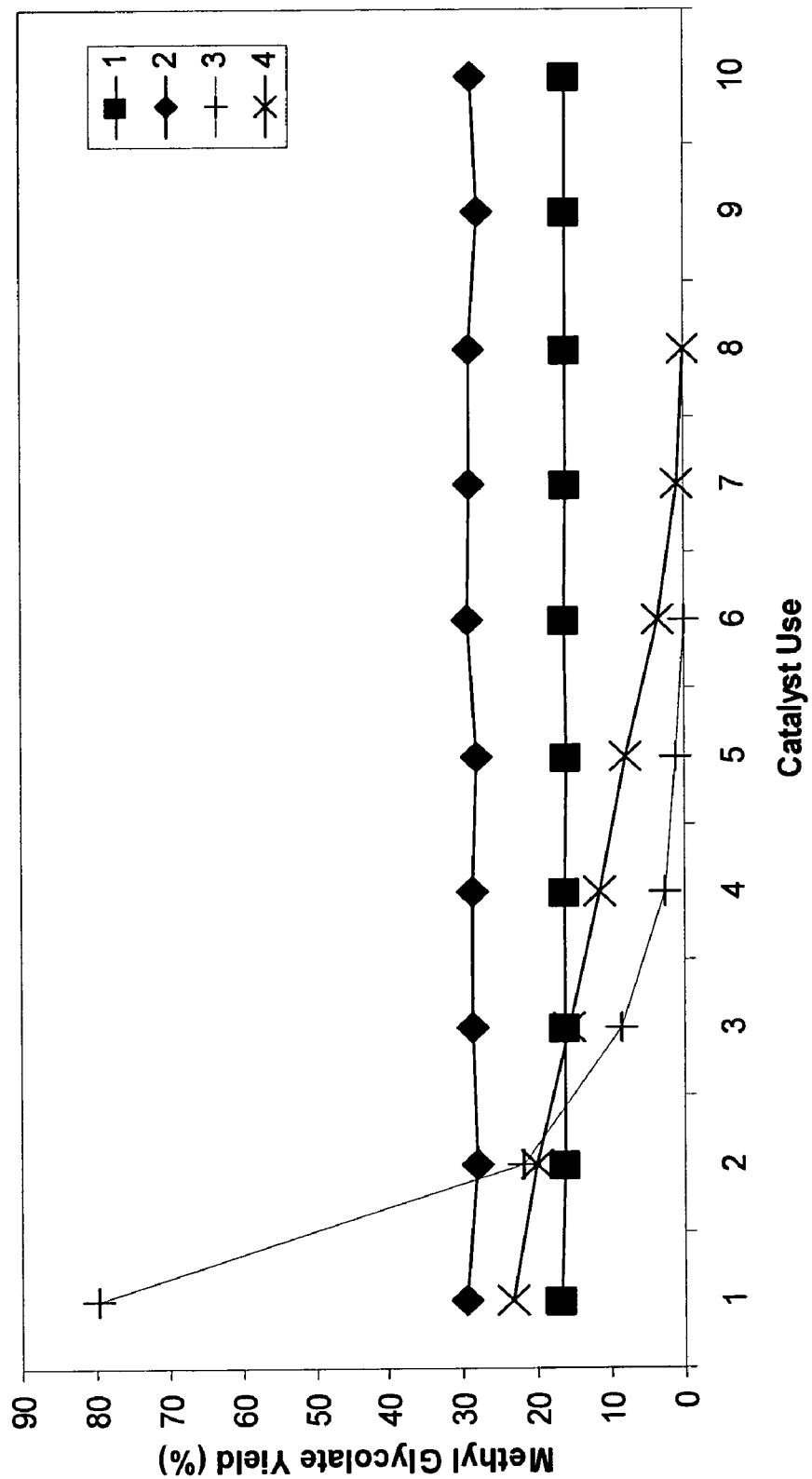

PROCESS FOR THE PRODUCTION OF GLYCOLIC ACID

This application is the U.S. national phase of International Application No. PCT/CN2008/000971, filed 20 May 2008, which designated the U.S., the entire contents of which is hereby incorporated by reference.

This invention relates to the production of glycolic acid, more specifically to the production of glycolic acid by carbonylation of formaldehyde.

BACKGROUND OF THE INVENTION

Ethylene glycol is a high volume and widely used chemical product, one of its main uses being in the production of polyester plastics and fibres. It is widely manufactured by the hydration of ethylene oxide, which itself is made by oxidation of ethylene.

An alternative method of producing ethylene glycol that avoids the need for an ethylene derivative, and consequently the need for a steam cracker to produce ethylene, is to use $C_1$ compounds as feedstock. Such processes include the reaction of carbon monoxide with formaldehyde, which results in the formation of glycolic acid, which can then be converted into ethylene glycol through processes such as hydrogenation, optionally after first being converted into a glycolic acid ester.

For example, He et al in Catalysis Today, 51 (1999), 127-134, describe the use of heteropolyacids as homogeneous catalysts for the carbonylation of formaldehyde or methyl formate.

U.S. Pat. Nos. 2,152,852 and 2,153,064 describe processes in which formaldehyde is contacted with an acidic catalyst and carbon monoxide, preferably with water, at elevated temperatures and pressures to produce glycolic acid. Inorganic and organic acids are stated to be suitable. In U.S. Pat. No. 2,153,064 pressures of 5 to 1500 atmospheres and temperatures of 50 to 350° C. are stated to be suitable.

U.S. Pat. No. 3,911,003 describes the production of hydroxyacetic acid (glycolic acid) from carbon monoxide, water and formaldehyde using a hydrogen fluoride catalyst. Temperatures of 0 to 100° C. and CO partial pressures of 10 to 4000 psig (1.6 to 273 atm) are stated to be suitable. The total pressure is stated as being only 1 to 10 percent higher than the CO partial pressure.

WO 01/49644 describes a process in which formaldehyde or a derivative thereof is reacted with carbon monoxide in the presence of an acid catalyst and a sulphone solvent, the acid catalyst having a pKa value of below −1. Halogenated sulphonic acids are stated to be preferred, although strongly acidic ion-exchange resins are also stated to be suitable as heterogeneous catalysts.

SUMMARY OF THE INVENTION

There remains a need for an alternative process for producing glycolic acid from $C_1$ reactants, and also a need for a process for producing glycolic acid from $C_1$ reactants in which the catalyst is resistant to leaching.

According to the present invention, there is provided a process for producing glycolic acid comprising contacting carbon monoxide and formaldehyde with a catalyst comprising an acidic polyoxometalate compound encapsulated within the pores of a zeolite, characterised by the zeolite having cages larger than the acidic polyoxometalate compound, and having pores with a diameter smaller than the diameter of the acidic polyoxometalate compound.

Polyoxometalate compounds comprise polyoxometalate anions, the structure of which are based on a plurality of condensed metal-oxide species. With protons as counter-ions, they exhibit Brønsted acidity. There are a number of known polyoxometalate structures, for example the Wells-Dawson, Anderson and Keggin forms. A description of polyoxometalate structures can be found in Catalysis for Fine Chemical Synthesis, Volume 2: Catalysis by Polyoxometalates, edited by I. Kozhevnikov, Springer-Verlag, Berlin, 2003. Common examples of acidic polyoxometalate compounds are heteropolyacids. Examples of heteropolyacids include silicotungstic acid, $H_4SiW_{12}O_{40}$, and phosphotungstic acid $H_3PW_{12}O_{40}$, which adopt the Keggin structure. Another example is iodomolybdic acid, $H_5Mo_6IO_{24}$, which adopts the Anderson structure. A further example is a different polymorph of phosphotungstic acid which adopts the Wells-Dawson structure, $H_6P_2W_{18}O_{62}$.

The acids are highly soluble in water and polar organic solvents, such as alcohols, ketones and aldehydes. They can be supported on insoluble solids, for example silica, alumina, aluminosilica, zirconia, ceria, titania, and carbon, to produce heterogeneous catalysts which can allow a high dispersion of heteropolyacid to be achieved. However, in liquid phase reaction compositions, for example formaldehyde carbonylation reaction compositions, there is a tendency for heteropolyacid to dissolve in the reaction mixture, which comprises polar formaldehyde and product glycolic acid, often in the presence of solvent.

It has now been found that the problems of leaching of the acidic polyoxometalate compounds can be reduced or even eliminated by encapsulating them within the cage structure of a zeolite, the zeolite having cages that are large enough to accommodate the polyoxometalate anion, and pores which intersect with the cages, and which are sufficiently small so that egress of polyoxometalate anions from the cages is prevented.

Zeolites are crystalline inorganic compounds with a porous structure. Often, where the pore structure involves intersecting channels in 2 or 3 dimensions, a cage is formed, the size of the cage being dependent on the size of the channels and the crystalline form of the zeolite. Most commonly, the zeolites comprise silica or aluminosilcate frameworks, although several other types exist such as aluminophosphates, silicoaluminophosphates, galloaluminates, gallophosphates and germanosilicates. The zeolites can also incorporate transition metal ions into the framework, for example titanium, cobalt and vanadium ions. Depending on the constituent elements, the framework can have a negative charge, which can be counter-balanced by non-framework cations. Where the cations are protons, the zeolite exhibits Brømsted acidity. However, other cations, for example ammonium, alkali-metal, alkaline-earth metal, transition metal and lanthanide cations can alternatively be used to counter the negative charge.

In the present invention, the catalyst comprises not only the acidic polyoxometalate compounds, but also a zeolite having a cage that is of sufficient size to accommodate the acidic polyoxometalate. Where the acidic polyoxometalate compound is held within the cage structure of the zeolite, demonstrable resistance to leaching and deactivation in formaldehyde carbonylation is observed.

A suitable zeolite that can be used in the present invention has a cage structure with a diameter larger than 10 Å, which can accommodate a polyoxometalate anion, while connected by channels or pores typically no larger than 8 Å in diameter, such that the polyoxometalate anion cannot diffuse out of the cage. One example of a suitable zeolite structure is the Faujasite structure (FAU), of which zeolite Y is an example. Full details of zeolite structures can be found in the Atlas of Zeolite Structure Types, available from the International Zeolite Association. Zeolite Y is an aluminosilicate zeolite comprising channels with 12-membered ring channel openings. By 12-membered ring channel opening is meant that the opening to the channel (or pore) is made up of 12 non-oxygen framework atoms, in this case Al and Si atoms. The channel diameter is about 7.4 Å. The channel structure is 3-dimensional, and has cages with a diameter of around 12.7 Å. Typically, zeolite Y has a silicon to aluminium molar ratio of greater than 1.5 and typically less than 100.

The cage structure of Zeolite Y is of sufficient dimension to accommodate polyoxometalate acids having the Keggin structure, while the diameter of the openings to the cages is too small to allow the polyoxometalate unit to leave the cage. By such means, the acidic polyoxometalate catalyst is prevented from leaching out of the zeolite support, and results in a catalyst with extended lifetime, particularly in liquid phase reactions.

An example of a polyoxometalate acid that can be used in the present invention is phosphotungstic acid, although partially neutralised salts thereof are also suitable. The Keggin form of phosphotungstic acid has a diameter of about 12 Å, which is smaller than the cage diameter of zeolite Y of 12.7 Å, and bigger than the pore diameter of about 7.4 Å.

Optionally, dealuminated forms of zeolites can be used. Dealumination treatment of a zeolite is typically carried out to partially disrupt the zeolite structure, which improves transport and diffusion of reactants and products of the reaction to and from the active catalytic sites in undisrupted portions of the zeolite structure. It is typically achieved by treatment with high temperature steam, and can result in removal of some of the framework aluminium. One form of "dealuminated" zeolite Y prepared by such a method is referred to as "USY" (ultra-stable Y). For non-dealuminated zeolite Y, the Si/Al mole ratio tends to be in the range of from 1.5 to 10, such as from 1.5 to 3. USY tends to have higher Si/Al mole ratios, for example 4 or more such as in the range of from 4 to 100, and is often in the range of from 4 to 40, such as 15 to 30.

Zeolites, such as zeolite Y, often comprise sodium as non-framework charge-balancing cations as a result of the synthetic procedures used to prepared them. The sodium form of the zeolites, for example the sodium form of zeolite Y, can be used in the catalyst of the process of the present invention without further treatment. However, this does not preclude the use of other cations. For example, the sodium ions could be exchanged in full or in part with smaller or larger cations to increase or decrease the bulk of cations within the zeolite cage, which would allow the accommodation of smaller or bigger polyoxometalate ions therein. Alternatively, the acidity of the catalyst can be modified by using partially or fully proton-exchanged zeolites. Exchange of zeolite non-framework cations is well known, and can be achieved through techniques such as ion exchange, involving suspension of the zeolite in a solution comprising the replament cation. Optionally, this procedure is carried out more than once to ensure ion-exchange is carried out to a sufficient extent. To prepare proton-exchanged zeolites, one technique is to replace fully or partially the non-framework cations with ammonium ions, and subsequently calcining the ammonium-exchanged zeolite.

In one embodiment, the catalyst are prepared by forming the polyoxometalate acid in situ within the zeolite pores. For example, in the case of phosphutungstic acid in zeolite Y, zeolite Y (or USY) can be loaded with a phosphate salt followed by a tungstate salt, and allowing the phosphotungstic acid to form, a proportion of which forms within the zeolite pores, which remains therein even after washing. Typically, the loading of polyoxometalate in the zeolite is in the range of from 0.1 to 50 wt % of the catalyst, for example in the range of from 1 to 30 wt %.

In one embodiment of the invention, the polyoxometalate acid is partially neutralised by one or more cations, such as ammonium or alkali or alkaline-earth metal cations, which enables some control over the acidity of the polyoxometalate acid to be achieved if desired.

In the process of the present invention, the catalyst is contacted with carbon monoxide and formaldehyde, optionally in the presence of a solvent. The reaction temperature is typically in the range of from 50 to 400° C., for example in the range of from 100 to 250° C. Pressures are typically in the range of from 1 to 1000 bara (0.1 to 100 MPa), such as in the range of from 1 to 200 bara (0.1 to 20 MPa).

The process can be a liquid-phase process, in which the reaction composition comprises a solvent. In one embodiment, the solvent is a sulphone, for example 2,3,4,5-tetrahydrothiophene-1,1-dioxide, often known as sulfolane. Water can optionally be present, either as the solvent or mixed with one or more other solvents.

Liquid phase processes can be conducted in a continuous flow configuration, which in one embodiment involves feeding the components of the reaction composition, i.e. carbon monoxide, formaldehyde and optional solvent, either premixed or separately, to a reactor comprising a fixed bed of catalyst, to produce a product composition which is continuously withdrawn from the reactor. Alternatively, the reaction can be conducted batch-wise, in which in one embodiment involves suspending and stirring a suspension of the catalyst in a liquid reaction composition comprising solvent and formaldehyde, with carbon monoxide being fed into the reactor under pressure. The resulting product composition can then be periodically removed from the reactor. Typically, any catalyst being removed from the reactor with the product stream is separated and fed back to the reactor to minimise catalyst loss.

The product composition comprises glycolic acid. The product composition can be treated to recover solvent and unreacted reactants, for example formaldehyde and carbon monoxide. This can be achieved by a variety of means. For example, formaldehyde and carbon monoxide can be recovered by flash separation and/or distillation.

Glycolic acid can be separated from the product composition by precipitation, for example by treatment with a salt such as a calcium salt, which converts the glycolic acid to an insoluble form which can then be separated by filtration, centrifugation or decantation. In another embodiment, the glycolic acid is treated with an alcohol, for example methanol or ethanol, to produce a glycolic acid ester which can be separated by distillation.

In one embodiment of the invention, the glycolic acid is converted to ethylene glycol.

This is typically achieved by hydrogenation of the glycolic acid, or a process stream comprising glycolic acid. In a further embodiment, the glycolic acid is first converted to an ester, for example a methyl or ethyl ester by reaction with methanol or ethanol respectively, which can then be hydrogenated to recover the alcohol and produce ethylene glycol (often also referred to as mono-ethylene glycol or MEG). The hydrogenation is typically carried out catalytically, using a conventional hydrogenation catalyst for example palladium, platinum, rhodium, ruthenium, cobalt or nickel on a support such as carbon, silica or alumina. Other catalysts include mixed oxides of copper and one or more of magnesium, manganese, nickel, iron, cobalt, chromium, calcium, barium, strontium, potassium, caesium, zinc, cadmium and silver. Hydrogenation of glycolic acid or glycolic acid ester is described in U.S. Pat. No. 2,285,448.

The source of carbon monoxide reactant can be a pure source of carbon monoxide, optionally comprising small quantities of impurities such as one or more of light alkanes, carbon dioxide or hydrogen. Alternatively, the carbon monoxide source can be a component of a gaseous mixture, for example syngas which is a mixture of hydrogen and carbon monoxide.

Formaldehyde reactant can be generated in situ within the reactor. For example, in one embodiment of the invention, paraformaldehyde is used as a reactant. Paraformaldehyde is a polymer of formaldehyde, which reverts to monomeric formaldehyde in the presence of polar molecules, such as water or alcohol solvents.

BRIEF DESCRIPTION OF THE DRAWINGS

There now follow non-limiting examples illustrating the invention, and with reference to FIG. 1 which is a graph showing the glycolic acid activity of supported phosphotungstic acid catalysts after repeated separation, washing and re-use.

EXAMPLE 1

Phosphotungstic acid was incorporated into a partially dealumiated zeolite Y (USY), by first adding 3 g USY (Si/Al mole ratio of 23) to a solution of 1.4 g sodium phosphate in 100 g water, and stirring the mixture at ambient temperature for 2 hours. A solution containing 8.6 g sodium tungstate was then added dropwise to the suspension and, after 1.5 hours of stirring, a stoichiometric quantity of 8.6 mL concentrated hydrochloric acid was added dropwise. The mixture was stirred for a further 4 hours, before filtering off the zeolite-supported phosphotungstic acid and drying at 383 K. The solid was suspended and agitated in hot water at a temperature of 353 K for one hour, and filtered. This hot water wash was carried out a total of ten times. The washing procedure removes phosphotungstic acid that is not encapsulated within the zeolite structure. The catalyst so prepared is represented henceforth as 10% PW-USY. The percentage loading (10 wt %) of phosphotungstic acid (PW) was calculated by comparing the weight of the USY used with the weight of the PW-loaded USY after washing and calcination in air at 500° C.

EXAMPLE 2

The procedure followed was the same as Example 1, but the loading of phosphotungstic acid was greater (represented henceforth as 25% PW-USY), and was prepared using 4.0 g of sodium phosphate, 25.0 g sodium tungstate and 25.0 mL concentrated hydrochloric acid.

COMPARATIVE EXAMPLE 3

Phosphotungstic acid was supported on the support SBA-15, which is a silica comprising a hexagonal array of mesoporous channels with diameters in the range of from 4.6 to 30 nm. 1 g of SBA-15 was suspended in a solution of 0.1 mmol phosphotungstic acid in 10 mL methanol. The suspension was stirred at room temperature for 3 hours. The resulting solid was filtered and evaporated to dryness at 100° C., and calcined in air at 500° C. for 4 hours. The phosphotungstic acid loading was 20 wt %. The non-encapsulated catalyst so prepared is represented henceforth as PW(NE)-SBA-15.

COMPARATIVE EXAMPLE 4

The procedure of Comparative Example 3 was followed, except that the support was USY. This is different from Examples 1 and 2, in that the phsophotungstic acid is supported on the external zeolite surface, and is not encapsulated within the pore and cage structure of the zeolite The phosphotungstic acid loading was 20 wt %. The non-encapsulated catalyst so prepared is represented henceforth as PW(NE)-USY.

Carbonylation experiments were carried out using a 100 mL stainless steel autoclave, which was lined with a Teflon™ liner. 1.0 g of catalyst was added to the autoclave, along with 0.2 g paraformaldehyde, 0.12 g water and 20 mL sulfolane solvent. The autoclave was purged with carbon monoxide (CO) three times, before finally being filled with CO to a pressure of 4.0 MPa (40 bara) and heating slowly to a reaction temperature of 120° C. The autoclave pressure at reaction temperature was estimated to be 5.4 MPa (54 bara). Reaction was continued for 4 hours.

The catalyst was reused, and was separated, washed with water and dried between experiments.

The reaction mixture filtrate was analysed using gas chromatography (GC). As glycolic acid is unstable under GC conditions, it was converted to the methyl ester before the GC analysis was conducted by adding 2.0 g methanol to the reaction mixture filtrate, and maintaining a temperature of 70° C. for 2 hours. After the esterification step, dimethylsulphoxide (DMSO) was added to product mixture as an internal standard Table 1 shows the results of glycolic acid yield (based on the quantity of methyl glycolate identified in the GC-analysis) for each use of the catalyst. It is clear that the encapsulated PW-USY catalysts show little or no signs of deactivation, even after several reaction cycles, whereas the SBA-15 and non-encapsulated PW-USY catalysts show deactivation with each re-use, indicating that the phosphotungstic acid is leaching from the support. No methyl glycolate was observed when polyoxometalate-free USY was used as a catalyst. The yields of methyl glycolate quoted in Table 1 are equivalent to glycolic acid yields.

The results are illustrated in FIG. 1, which show the maintenance of catalytic activity with re-use for the encapsulated polyoxometalate catalysts, as opposed to a decline in activity with reuse for the non-encapsulated polyoxometalate catalyst. In FIG. 1, the labels relate to samples prepared according to the corresponding Examples and Comparative Examples.

TABLE 1

Methyl Glycolate Yield.

| Catalyst | Methyl Glycolate Yield (%) for successive catalyst re-use. | | | | | | | | | |
|---|---|---|---|---|---|---|---|---|---|---|
| | 1 | 2 | 3 | 4 | 5 | 6 | 7 | 8 | 9 | 10 |
| 10% PW-USY | 16.7 | 16.2 | 16.3 | 16.1 | 16.0 | 16.1 | 16.0 | 15.9 | 16.0 | 15.8 |
| 25% PW-USY | 29.4 | 27.9 | 28.7 | 28.5 | 28.1 | 29.2 | 29.0 | 28.8 | 27.8 | 28.6 |

TABLE 1-continued

Methyl Glycolate Yield.

| Catalyst | Methyl Glycolate Yield (%) for successive catalyst re-use. | | | | | | | | | |
|---|---|---|---|---|---|---|---|---|---|---|
| | 1 | 2 | 3 | 4 | 5 | 6 | 7 | 8 | 9 | 10 |
| PW(NE)-USY | 79.8 | 21.7 | 8.6 | 2.7 | 1.2 | 0 | — | — | — | — |
| PW(NE)-SBA-15 | 23.4 | 20.0 | 15.7 | 11.5 | 7.9 | 3.5 | 1 | 0 | — | — |

The invention claimed is:

1. A process for the production of glycolic acid comprising contacting carbon monoxide and formaldehyde with a catalyst comprising an acidic polyoxometalate compound encapsulated within the pores of a zeolite, wherein the zeolite has cages larger than the acidic polyoxometalate compound, and has pores with a diameter smaller than the diameter of the acidic polyoxometalate compound.

2. A process as claimed in claim 1, in which the zeolite has cages with a diameter of larger than 10 Å, and the pores have a diameter of no larger than 8 Å.

3. A process as claimed in claim 1, in which the zeolite has the FAU structure.

4. A process as claimed in claim 3, in which the zeolite is zeolite Y or zeolite USY.

5. A process as claimed in claim 1, in which the polyoxometalate compound is a heteropolyacid, or partially neutralised heteropolyacid.

6. A process as claimed in claim 5, in which the polyoxometalate compound is phosphotungstic acid.

7. A process as claimed in any one of claim 1, in which the process is a liquid phase process, the process being carried out in the presence of a solvent.

8. A process as claimed in claim 7, in which the solvent is a sulphone or a combination of a sulphone and water.

9. A process as claimed in claim 7, in which the reaction temperature is in the range of from 50 to 400° C., and the pressure is in the range of from 1 to 1000 bara (0.1 to 100 MPa).

10. A process as claimed in claim 1, in which the glycolic acid product is converted into ethylene glycol.

11. A process as claimed in claim 10, in which the glycolic acid product is converted into ethylene glycol through hydrogenation.

12. A process as claimed in claim 11, in which the glycolic acid is first converted to an ester by reaction with an alcohol before being hydrogenated to ethylene glycol.

* * * * *